United States Patent [19]

Shaw

[11] Patent Number: 5,653,244
[45] Date of Patent: Aug. 5, 1997

[54] THERAPEUTIC COMPRESSION GARMENT

[75] Inventor: Sandra Anne Shaw, Coronado, Calif.

[73] Assignee: Circaid Medical Products, Inc., San Diego, Calif.

[21] Appl. No.: 658,519

[22] Filed: Jun. 4, 1996

[51] Int. Cl.⁶ .................................................. A61F 5/37
[52] U.S. Cl. ........................... 128/882; 128/DIG. 15; 602/62
[58] Field of Search ........................ 128/846, 878, 128/879, 882, DIG. 15, DIG. 20; 602/5, 20, 23, 60, 61, 62

[56] References Cited

U.S. PATENT DOCUMENTS

| | | | |
|---|---|---|---|
| 3,298,366 | 1/1967 | Moore | 128/169 |
| 3,538,914 | 11/1970 | Myers | 128/DIG. 15 |
| 3,845,769 | 11/1974 | Shaw | |
| 4,215,687 | 8/1980 | Shaw | 128/DIG. 15 |
| 5,254,122 | 10/1993 | Shaw | 606/201 |

Primary Examiner—Michael A. Brown
Attorney, Agent, or Firm—Harris F. Brotman

[57] ABSTRACT

A therapeutic compression garment made of flexible, foldable, light weight Velcro-type loop fabric having a central region for wrapping partially around a body part and a plurality of pairs of bands integrally connected to the central region and extending outwardly in opposite directions from both sides of the central region to encompass the body part.

13 Claims, 4 Drawing Sheets

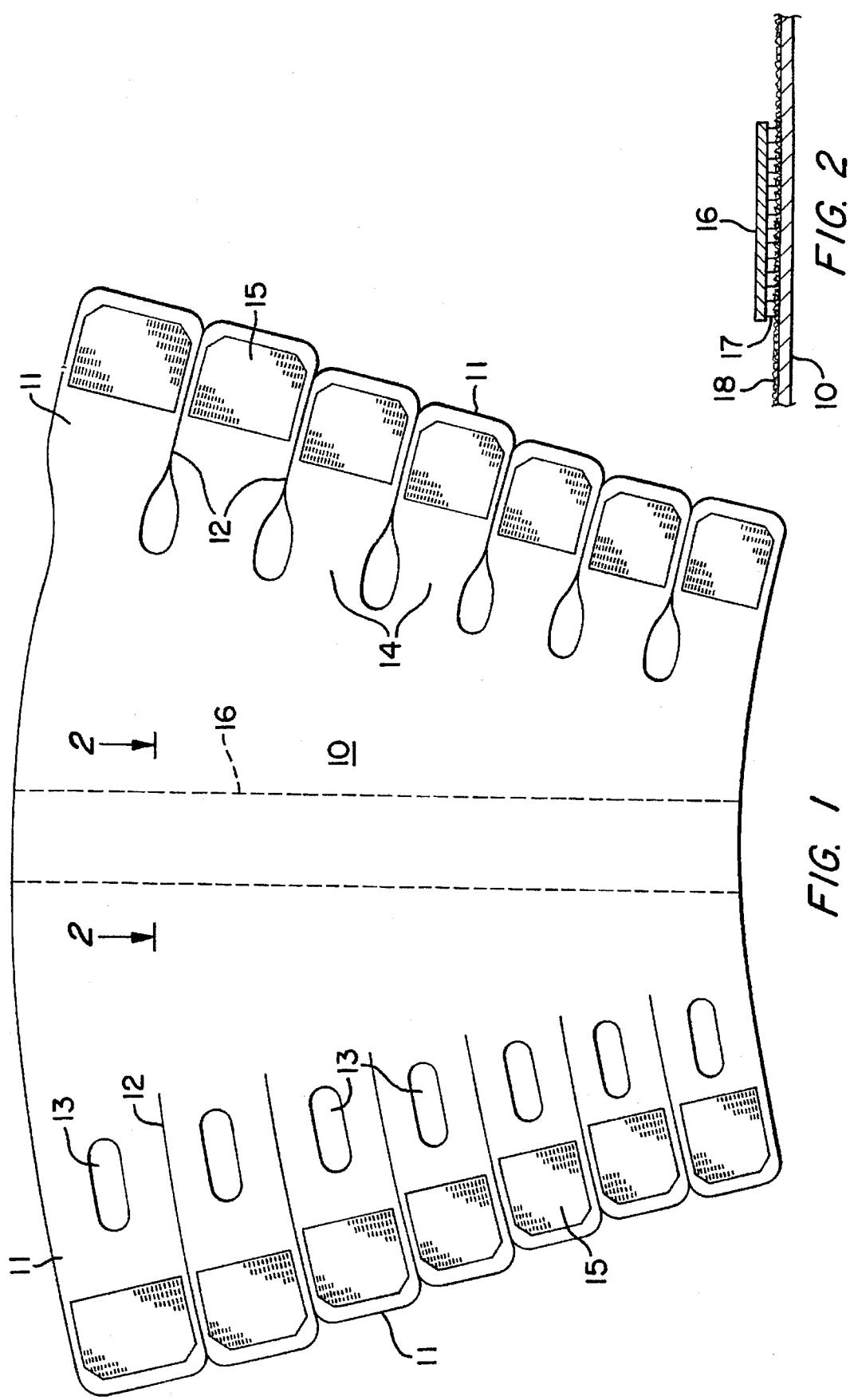

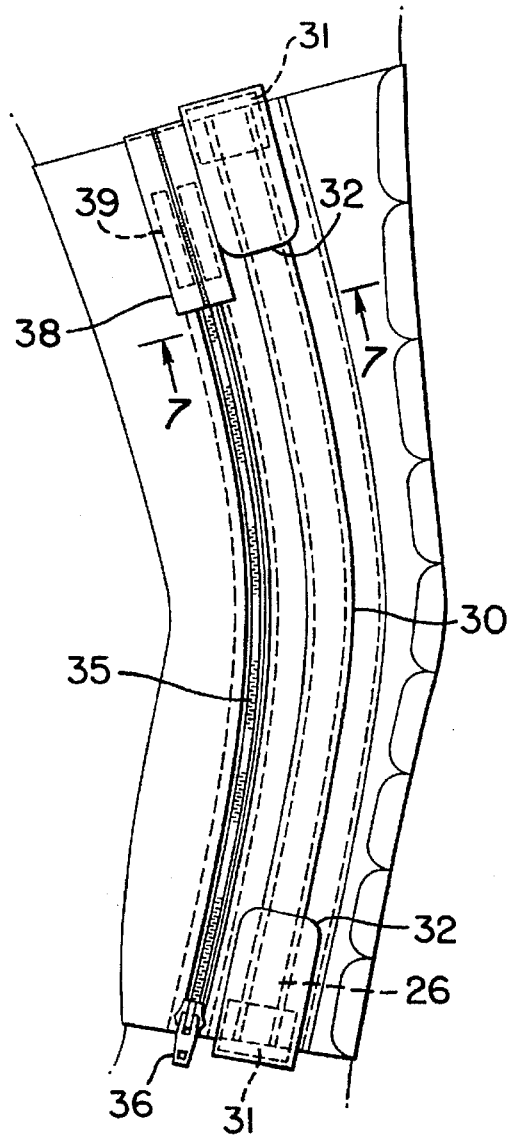
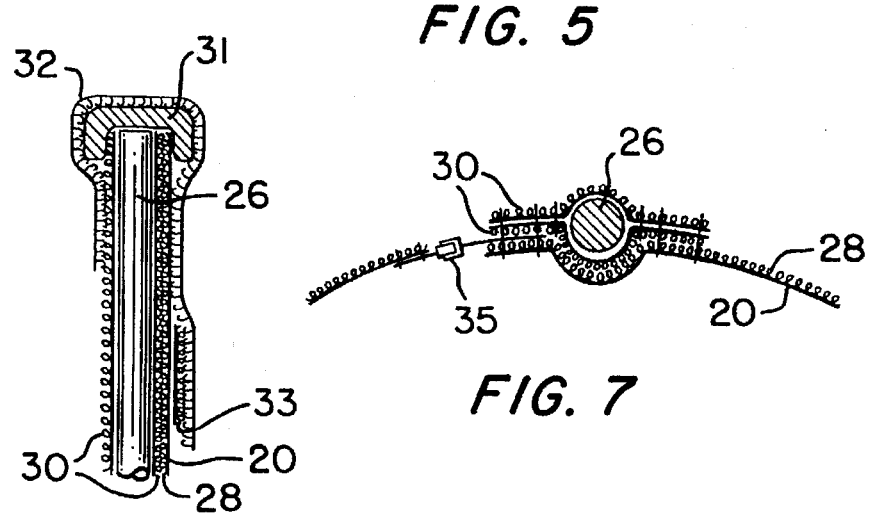

THERAPEUTIC COMPRESSION GARMENT

BACKGROUND OF THE INVENTION

This invention relates to a novel therapeutic garment for applying an adjustable, sustainable, essentially inelastic compression to a part of the body, such as a limb.

Elastic and inelastic anklets and stockings have been employed in compression therapy of the limbs. Most suffer various degrees of shortcomings, particularly in effectiveness, difficulties in application and removal, lack of adjustability, loss of compression and discomfort.

U.S. Pat. No. 3,845,769 relates to a boot having a split sleeve of essentially unyielding material shaped to fit a leg. The sleeve is held in position and compression is applied by a plurality of bands of interlocking fabric material, such as Velcro or Scotchmate.

U.S. Pat. No. 4,215,687 relates to a combination or kit which permits the in situ construction and assembly of a therapeutic compression device directly on the patient by a doctor or other skilled person. The combination or kit includes a Velcro-type anchoring tape having an interlocking fabric material on one side and a plurality of body or limb encircling Velcro-type bands which are assembled, one by one, in edge-to-edge relationship either by direct contact with the anchoring tape or by indirect contact through Velcro-type splicing means. These custom-made therapeutic compression devices have achieved wide recognition in healing leg ulcers and in the treatment of lymph edema. On the other hand, the custom construction which requires splicing of the body or limb encircling bands when they are too long and when the portion of the body or limb is contoured is a tedious and time consuming task.

U.S. Pat. No. 5,120,300 relates to a compression band for use in the therapeutic device disclosed in U.S. Pat. No. 4,215,687 and, more particularly, to a compression band for quick and easy application to and removal from a body part.

U.S. Pat. No. 5,254,122 relates to a therapeutic compression device of the type disclosed in U.S. Pat. No. 4,215,687 which includes a longitudinally extending splicing band or slide fastener which facilitates quick and easy removal of the device from the body or limb and quick and easy reapplication to the body or limb without the necessity of unthreading the adjusted compression bands.

SUMMARY OF THE INVENTION

The present invention relates to a therapeutic garment for applying compression to a part of the body, such as a limb. The garment is made from a flexible, foldable, light weight Velcro-type loop fabric which, due to its inherent characteristics, can be prefabricated in different sizes and need not be custom-made in situ on the wearer.

The therapeutic compression garment of the present invention includes a plurality of pairs of body or limb encircling bands integrally connected to a central wrap around region and extending outwardly in opposite directions from both sides of the central region to encompass the body part. A slot in one of the bands in each pair accommodates the opposite band in threaded, folded relationship and Velcro-type hook surfaces on the inner surfaces at or near the ends of each pair make it possible to tighten the pairs of bands to apply the desired compression and to maintain that compression by pressing the inner hook surfaces of the band ends against the outer loop surface of the garment to anchor the bands in tightened condition.

The therapeutic garment of the present invention represents a significant advance over the custom-made therapeutic device of U.S. Pat. No. 4,215,687 in that several off-the-shelf stock sizes fit all but the very unusual limb, custom fitting is eliminated, labor and material costs are significantly reduced and the garment is less bulky, lighter in weight, more comfortable and more cosmetic.

The therapeutic garment of the present invention can be made from a single piece of flexible, foldable Velcro-type fabric having a outer loop surface. Alternatively, the central region of the garment can be equipped with a longitudinally extending slide fastener to separate portions of the one piece garment to facilitate quick removal and quick reapplication of the garment to the body part without unthreading the bands which apply the desired compression.

Because the fabric is of lighter weight and more readily flexible and foldable than the thicker, heavier and more rigid material used in the prior art custom-made therapeutic compression device described above, it is desirable to stiffen or reinforce the central region longitudinally of the garment to prevent wrinkling, collapsing or slippage of the upper portion of the garment relative to the lower portion. This can be accomplished by various suitable means, such as a narrow band of Velcro-type band having an inner hook surface which can be anchored against the outer loop surface of the garment or by a longitudinally extending flexible rod affixed to the outer surface of the central region of the garment. Use of one or more flexible rods as a reinforcement device is of particular advantage in therapeutic compression garments which extend across the knee or elbow because they will readily deflect when the knee or elbow is bent while providing the desired reinforcement.

For a more complete understanding of the present invention reference can be made to the detailed description which follows and to the accompanying drawings.

DESCRIPTION OF THE DRAWINGS

FIG. 1 is a view of the inner surface of a therapeutic compression garment of the present invention;

FIG. 2 is a sectional view taken along the line 2—2 of FIG. 1 looking in the direction of the arrows;

FIG. 5 is a view of the therapeutic compression garment shown in FIGS. 3 and 4 applied to a leg;

FIG. 6 is cross sectional view taken along the line 6—6 of FIG. 3 looking in the direction of the arrows; and FIG. 7 is a view taken along the line 7—7 of FIG. 5 looking in the direction of the arrows.

DESCRIPTION OF PREFERRED EMBODIMENTS

Figure 3:
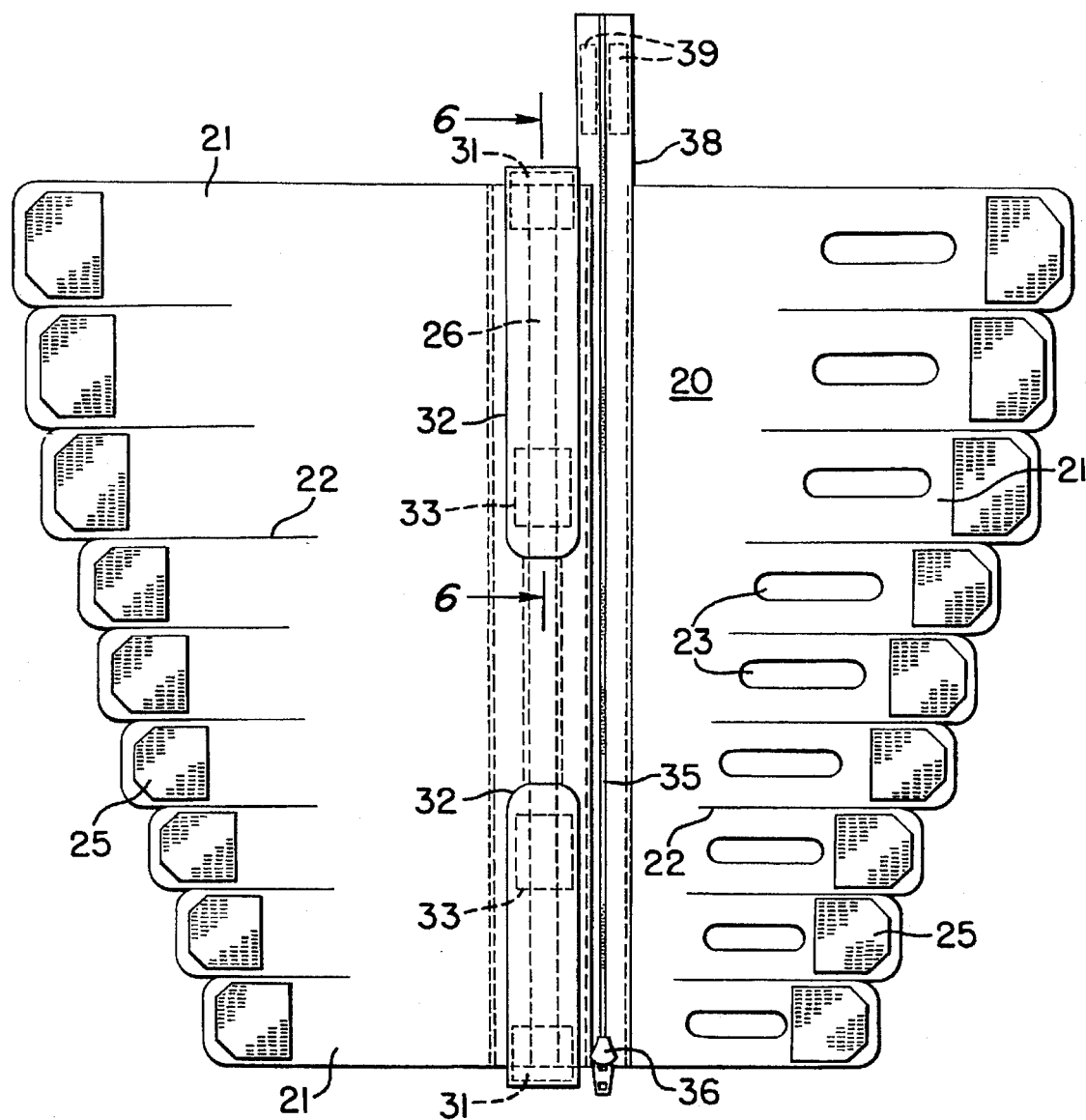
FIG. 3 is a view of the inner surface of another embodiment of the therapeutic compression garment of the present invention.

The therapeutic compression garment shown in FIG. 1 is made in one piece from a flexible, foldable Velcro-type fabric having an outer loop surface which is preferably a light weight loop fabric of the type designated Velcro 3610 or Velcro 3800, the former being substantially inelastic and the latter having a limited stretch at least in the vertical or longitudinal direction.

The therapeutic garment of FIG. 1 includes a central region 10 which is wrapped around the body part and a plurality of pairs of bands 11 integrally connected to the central region and extending outwardly in opposite directions from both sides of the central region to encompass the body part. The bands 11 are defined by slits 12. One of the bands of each pair includes a slot 13 to accommodate the opposite band in threaded, folded relationship to apply compression to the body part encompassed by the garment. The bands which are threaded through the slots 13 may include portions 14 of reduced width formed by widening the slits separating the bands, but such narrow width portions are not essential because of the flexible, foldable characteristics of the fabric. The inner surfaces of the bands have Velcro-type hook surfaces 15 at or near their ends. The opposite bands of each pair are extended toward each other and one band of each pair is threaded through the slot in the other band of the pair and then tightened to apply the desired compression to the body part. The inner hook surfaces 15 are then pressed against the outer loop surface 18 of the fabric to anchor the bands in tightened condition. The garment is removed by separating the hook surfaces 15 of the bands from the outer loop surface of the garment and then unthreading the bands.

In order to facilitate handling the fabric during application to the body part and to prevent wrinkling of the fabric or slippage of the upper end of the garment relative to the lower end, the fabric is preferably stiffened or reinforced longitudinally, such as by a strip, rod or other suitable means. In the therapeutic garment shown in FIG. 1 and as best shown in FIG. 2, such reinforcement is provided by a longitudinal band 16 of Velcro-type fabric having an inner hook surface 17 which adheres to the outer loop surface 18 of the garment. The strip is preferably a high shear hook tape, such as Velcro P87 affixed along the vertical center line of the central region 10 of the garment to stiffen it and prevent possible wrinkling.

The therapeutic garment of this invention does not have to be custom-made to the body part because the fabric readily conforms to the body contour due to its inherent characteristics, such as light weight, flexibility and foldability, in contrast to the heavier, thicker and more rigid materials used in the therapeutic device described in U.S. Pat. No. 4,215,687. In the therapeutic garment of the present invention, some overlap of the bands can be tolerated without creating gaps or spaces in the compression applied to the body part. The Velcro knit loop 3800 fabric is particularly advantageous in that its limited stretch characteristics permit it to shape, mold and conform to the body, particularly in the knee and elbow regions, while applying an inelastic compression to the body part due to the fact that the stretch limit is exceeded in tightening the bands before the desired compression levels are reached. The Velcro knit loop 3800 fabric is a nylon multifilament yarn of 28 gage knit construction having specifications as follows: weight: 9.70 oz. per sq. yd.; thickness: 0.060 inches; peel strength (w/hook 88): 1.30 plw; shear strength (w/hook 88): 27.49 psi; tension strength (W/hook 88): 10.56 psi; break strength (machine direction): 69.1 lbs.; shrinkage: 3% max; curl: 6.25% max; stiffness: 2.5 inch min.; fabric stretch for 5 lb. force applied to band: 5.5% in the cross machine or longitudinal direction of garment and 2.5% in the machine or horizontal direction of garment. The fabric is oriented in the garment such that the greater stretch is in the longitudinal or vertical direction of the garment and the lesser stretch is in the transverse or horizontal direction of the garment.

In the therapeutic compression garment shown in FIG. 1 for use on a leg above or below the knee and made of a relatively inelastic material, such as Velcro 3610 loop fabric, the central region 10 is wider at the top than at the bottom and the pairs of limb compression bands are longer at the top than the pairs of limb compression bands at the bottom. The pairs of limb compression bands are separated from adjacent pairs of limb compression bands by slits 12 which extend downwardly in opposite directions at angles of about 15°±10% from the longitudinal middle of the central region to minimize overlap of the compression bands applied to the leg. The garment can be shortened longitudinally by cutting off upper or lower pairs of bands.

Figure 4:
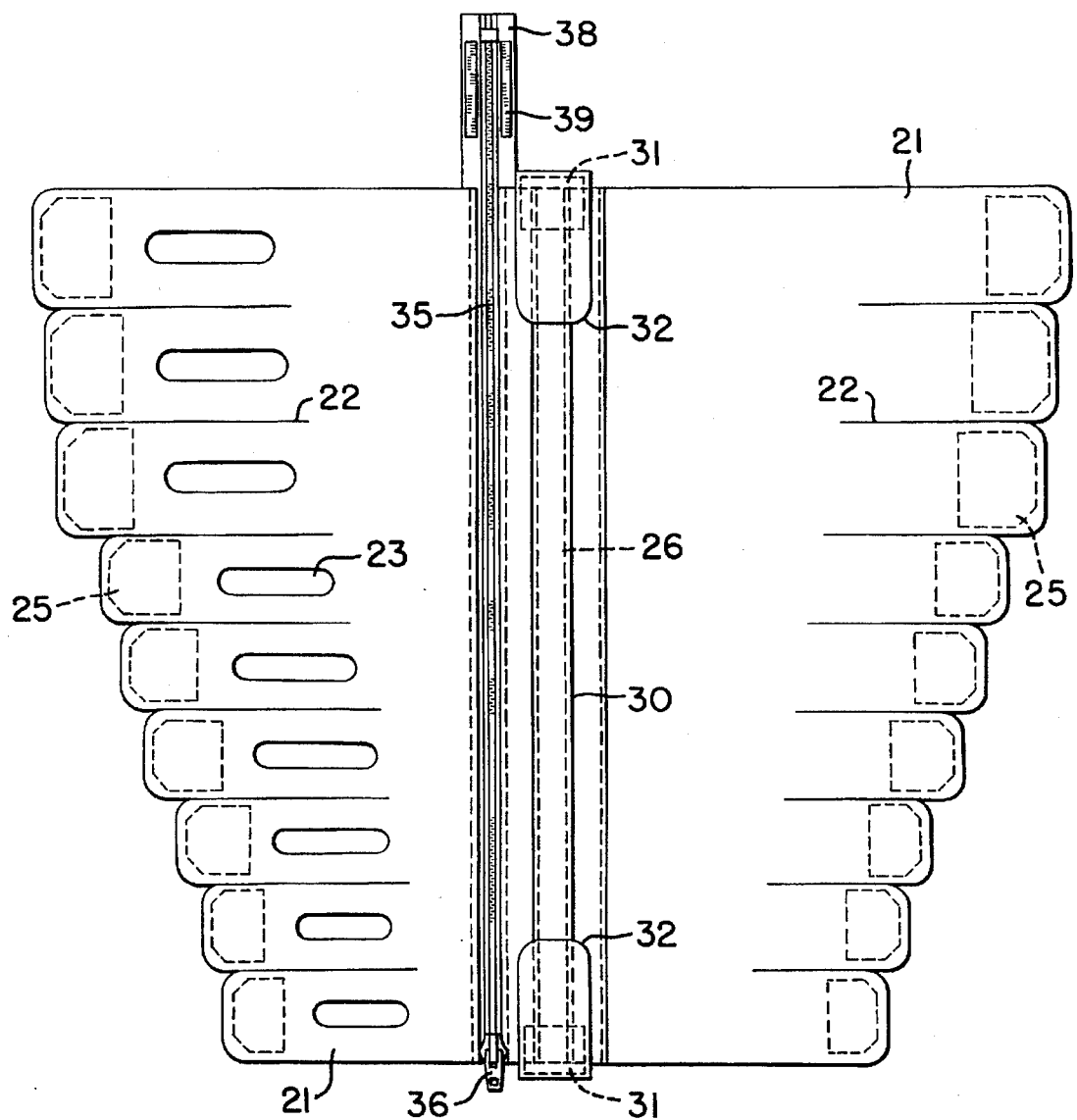
FIG. 4 is a view of the outer surface of the therapeutic compression garment shown in FIG. 3.

The therapeutic compression garment of FIGS. 3 and 4 is preferably made of a limited stretch fabric, such as Velcro 3800 loop fabric, having an outer loop surface 28 (see FIGS. 6 and 7). The fabric is oriented in the garment with the greater stretch in the longitudinal direction and the lesser stretch in the transverse direction. The garment has a central region 20 for wrapping partially around the body part and a plurality of pairs of bands 21 integrally connected to the central region and extending outwardly in opposite directions from both sides of the central region to encompass the body part. The bands 21 are defined by parallel slits 22 which are arranged at about 90° from the longitudinal direction of the garment. Transversely extending slots 23 are provided in one of the bands of each pair to accommodate the opposite band in threaded, folded relationship, and Velcro-type hook surfaces 25 are carried at the ends or near the ends on the inner surfaces of each pair of bands.

In applying the therapeutic compression garment on a body part, such as a region extending from above the knee to the ankle, the opposite bands of each pair are extended toward each other and one band of each pair is threaded through a slot in the other band of the pair and then tightened to apply the desired compression. The inner hook surfaces are pressed against the outer loop surface of the garment to anchor the bands in tightened condition.

In order to stiffen or reinforce the garment and prevent it from collapsing or wrinkling during application, a longitudinal bendable or flexible rod is mounted against the outer surface of the garment as shown in FIG. 7. The rod, for example, a cylindrical silicon rubber rod, is accommodated in a pocket 30 having an outer loop surface sewn to the outer loop surface 28 of the central region 20 of the garment. To prevent irritation to the skin of the wearer of the garment, a cushioning pad 31 is held in place at each end of the rod 26 by suitable means, such as a strip 32 of Velcro-type fabric having an inner hook surface which adheres at one end to the outer loop surface 28 of the garment and at the other end to a patch of loop surface material 33 fixed to the inner surface of the garment.

A longitudinally extending slide fastener or zipper 35 extends at least the longitudinal length of the central region 20 of the garment to facilitate removal and reapplication of the garment without unfastening the bands. In the therapeutic compression device shown in FIGS. 3 and 4 for use on a leg, the runner 36 closes the slide fastener during its longitudinal movement from the upper end of the garment to the lower end of the garment and opens the slide fastener during its upward return movement. When the garment is applied to an arm, the direction of the closure of the runner 36 is reversed because starting the zipper closure requires both hands, and it would be virtually impossible to attach and start the zipper at the top of the arm.

In the preferred embodiment of the therapeutic compression garment shown in FIGS. 3 and 4, the slide fastener extends at one end beyond the upper or lower end of the central region of the garment to permit separation of the central region along its entire length while the separated portions of the central region remain connected by the extreme end of the extended portion of the slide fastener. The extended portion 38 shown in FIG. 3 permits the runner 36 to slide upwardly to open the slide fastener beyond the upper edge of the central region of the garment to facilitate removal of the garment from the body part and reapplication thereof. In this way the garment can be removed and replaced by loosening and without unthreading the compression bands. The upward movement of the slide 36 is limited so that the separated portions of the central region of the garment remain connected by the end of the extended portion of the slide fastener. The extension 38 has a strip of hook tape 39 along each of its outer cloth edges to hold it against the outer loop surface of the garment in its folded down position shown in FIG. 5.

A flap (not shown) may be provided to cover the slide fastener and the folded down zipper extension 38. If provided, the strips 39 of hook tape can be omitted. In the alternative, the outer surface of the flap can be provided with a Velcro-type loop surface and the extension 38 and the hook surface strips can be folded over the flap and adhered thereto. The flap would contribute to the needed stiffening and wrinkling resistance provided by the longitudinally extending rod 26.

The therapeutic compression garment shown in FIGS. 3 and 4 equipped with a longitudinally extending stiffening rod 26 and longitudinally extending slide fastener 35 would preferably be worn such that the stiffening rod and slide fastener are located on the inside or outside of a limb to facilitate opening and closing the slide fastener and to prevent the stiffening rod from interfering with the bending of the knee or elbow. In this way, the stiffening rod flexes with the bending of the knee or elbow without undue wrinkling or distortion of the garment.

The invention has been shown in preferred forms and by way of example, and many variations and modifications can be made therein within the spirit of the invention. The invention, therefore, is not intended to be limited to any specified form or embodiment, except insofar as such limitations are expressly set forth in the claims.

I claim:

1. A therapeutic garment for applying compression to a part of the body comprising a unitary piece of flexible, foldable, light weight hook and loop fastener fabric having an outer loop surface and an inner surface comprising a central region for wrapping partially around the body part, wherein slits formed in the outer edge of said garment form a plurality of pairs of bands, said bands integrally connected to the central region and extending outwardly in opposite directions from both sides of the central region to encompass the body part, a slot in one of the bands of each pair to accommodate the opposite band in threaded, folded relationship and hook and loop fastener surfaces at the ends of the inner surfaces of each pair of band, whereby the opposite bands of each pair can be extended toward each other and one band of each pair can be threaded through the slot in the other band of the pair and tightened to apply the desired compression and their inner hook surfaces can be pressed against the outer loop surface to anchor the bands in tightened condition.

2. A therapeutic compression garment as set forth in claim 1 in which the central region is wider at the top than at the bottom and the pairs of compression bands are longer at the top than the pairs of compression bands at the bottom.

3. A therapeutic compression garment as set forth in claim 1 in which the pairs of compression bands are separated from adjacent pairs of compression bands by slits which extend downwardly in opposite directions at angles from the longitudinal middle of the central region to minimize overlap of the compression bands applied to the body part.

4. A therapeutic compression garment as set forth in claim 1 in which the garment is substantially inelastic with a slight amount of stretch at least in the longitudinal direction of the garment.

5. A therapeutic compression garment as set forth in claim 1 in which the pairs of compression bands are separated from adjacent pairs of bands by substantially parallel slits which extend outwardly from the central region of the garment.

6. A therapeutic compression garment as set forth in claim 1 including a stiffening means extending longitudinally in the central region to prevent wrinkling and slippage of the upper end of the garment relative to the lower end when applied to the body part.

7. A therapeutic compression band as set forth in claim 6 in which the stiffening means is a longitudinal band having a hook and loop fastener surface adhered to the outer hook and loop fastener surface of the garment.

8. A therapeutic compression garment as set forth in claim 6 in which the stiffening means is a longitudinal bendable rod held against the outer surface of the garment.

9. A therapeutic device as set forth in claim 8 including a cushion held in place at at least one end of the rod.

10. A therapeutic garment as set forth in claim 1 including a longitudinally extending slide fastener in the central region of the garment to facilitate removal from or reapplication to the body part without undoing the bands.

11. A therapeutic garment as set forth in claim 10 in which at least one end of the slide fastener extends beyond the central region of the garment to permit separation of the central region along its entire length while the separated portions of the central region remain connected by the extended portion of the slide fastener.

12. A therapeutic garment as set forth in claim 11 including means for holding the extended portion of the slide fastener in folded down position against the outer surface of the garment.

13. A therapeutic garment as set forth in claim 10 including a flap covering the slide fastener.

* * * * *